United States Patent
Rohr, Jr.

Patent Number: 5,474,560
Date of Patent: Dec. 12, 1995

[54] PROSTHETIC ACETABULAR CUP INSERTER

[75] Inventor: William L. Rohr, Jr., Warsaw, Ind.

[73] Assignee: Zimmer, Inc., Warsaw, Ind.

[21] Appl. No.: 312,380

[22] Filed: Sep. 26, 1994

[51] Int. Cl.$^6$ .................................................. A61B 17/56
[52] U.S. Cl. ........................... 606/91; 606/99; 606/104
[58] Field of Search .................................. 606/91, 86, 99, 606/100, 104, 89; 623/18, 22, 23; 269/1, 3, 47, 48, 52

[56] References Cited

U.S. PATENT DOCUMENTS

| | | |
|---|---|---|
| 3,859,992 | 1/1975 | Amstutz . |
| 3,892,232 | 7/1975 | Neufeld ............................. 606/104 X |
| 4,305,394 | 12/1981 | Bertuch, Jr. . |
| 4,342,309 | 8/1982 | Eftekhar ............................. 606/104 X |
| 4,475,549 | 10/1984 | Oh . |
| 4,476,861 | 10/1984 | Dimakos et al. . |
| 4,528,980 | 7/1985 | Kenna . |
| 4,632,111 | 12/1986 | Roche . |
| 4,716,894 | 1/1988 | Lazzeri et al. ........................ 606/91 X |
| 5,037,424 | 8/1991 | Aboczsky ................................. 606/91 |
| 5,116,339 | 5/1992 | Glock ........................................ 606/91 |
| 5,171,243 | 12/1992 | Koshuba et al. .......................... 606/86 |
| 5,354,300 | 10/1994 | Goble et al. ............................. 606/80 |
| 5,364,403 | 11/1994 | Peterson et al. ......................... 606/91 |

*Primary Examiner*—Stephen C. Pellegrino
*Assistant Examiner*—Guy V. Tucker
*Attorney, Agent, or Firm*—Todd A. Dawson

[57] ABSTRACT

The insertion instrument of this invention includes a generally cylindrical handle portion and a cup engaging portion held in a spaced relationship by an arcuate intermediate portion. Handle portion includes a longitudinal throughbore and an impaction head. The cup engaging portion includes a rotatable threaded stud for threaded accommodation within a threaded hole of an prosthetic acetabular cup. The stud includes a head having a recess formed therein for accommodating a driving device. The longitudinal bore of the handle portion and the head of the threaded stud are placed in alignment such that the shaft of a screwdriver extending through the threaded bore is aligned with the head of the screw. Therefore, a surgeon using the instrument of this invention does not need to have a clear view of the threaded stud to attach a screw driver. This is especially useful after the surgeon has impacted the acetabular cup within a prepared acetabulum and needs to remove the insertion instrument. Often, the head of the screw may be obscured from the surgeon by the depth of the wound. This instrument provides for the easy alignment of the driver and the head of the threaded stud.

4 Claims, 1 Drawing Sheet

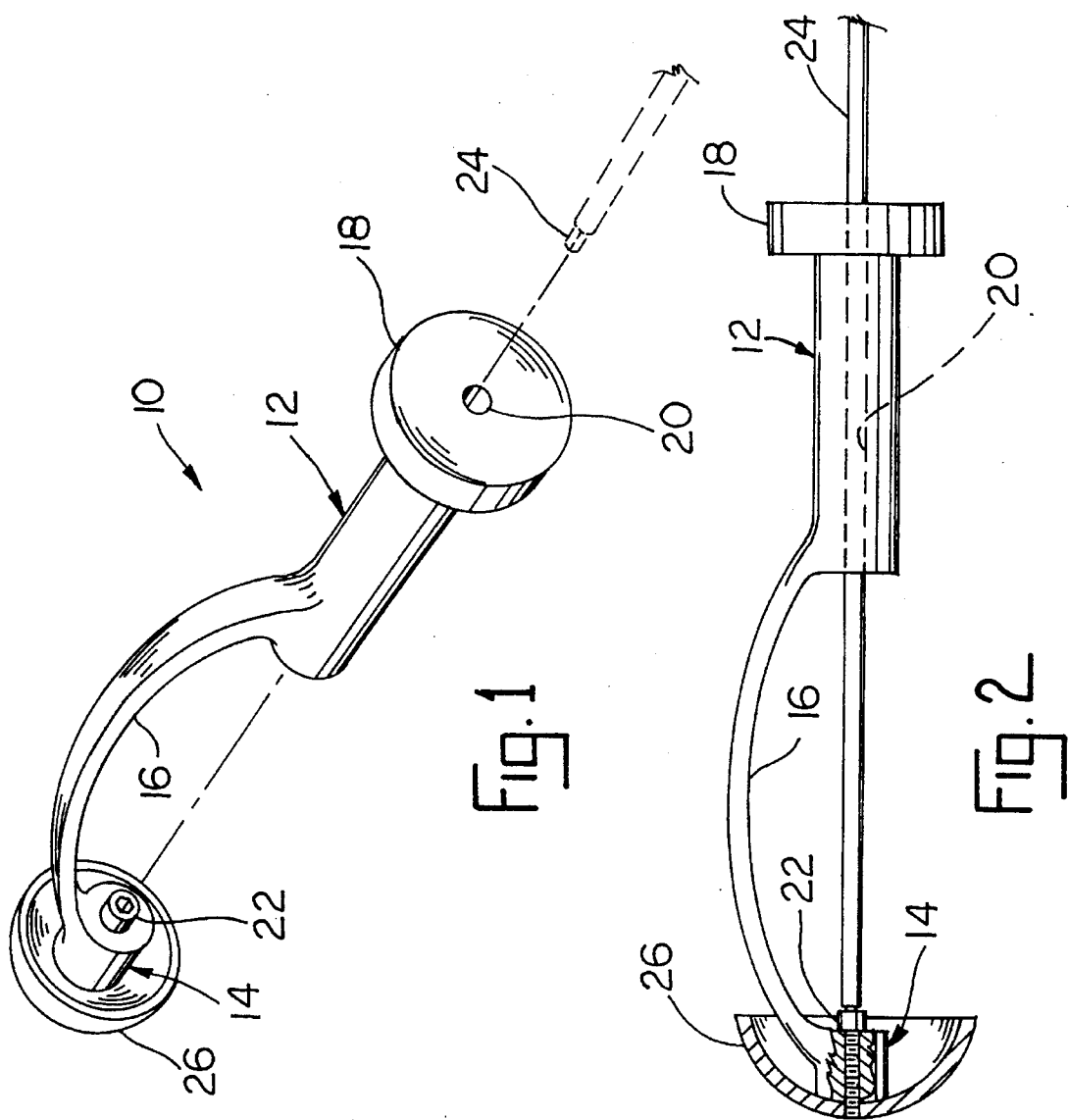

PROSTHETIC ACETABULAR CUP INSERTER

FIELD OF THE INVENTION

This invention relates to an orthopaedic instrument for inserting a prosthetic acetabular cup and has specific relevance to a cup insertion instrument wherein the handle aligns a screwdriver with a distal spaced connection screw.

SUMMARY OF THE INVENTION

The insertion instrument of this invention includes a generally cylindrical handle portion and a cup engaging portion held in a spaced relationship by an arcuate intermediate portion. Handle portion includes a longitudinal throughbore and an impaction head. The cup engaging portion includes a rotatable threaded stud for threaded accommodation within a threaded hole of an prosthetic acetabular cup. The stud includes a head having a recess formed therein for accommodating a driving device. The longitudinal bore of the handle portion and the head of the threaded stud are placed in alignment such that the shaft of a screwdriver extending through the threaded bore is aligned with the head of the screw. Therefore, a surgeon using the instrument of this invention does not need to have a clear view of the threaded stud to attach a screwdriver. This is especially useful after the surgeon has impacted the acetabular cup within a prepared acetabulum and needs to remove the insertion instrument. Often, the head of the screw may be obscured from the surgeon by the depth of the wound. This instrument provides for the easy alignment of the driver and the head of the threaded stud.

Accordingly, it is an object of this invention to provide a novel insertion instrument for an orthopaedic instrument.

Another object of this invention is to provide for an acetabular insertion tool wherein the handle portion acts as a guide for a driver device to align the driver device with the distal end of the instrument.

Other objects of the invention will become apparent upon a reading of the following description taken with the accompanying drawings.

BRIEF DESCRIPTION OF THE DRAWINGS

FIG. 1 is a perspective view of the insertion instrument of the invention as connected to an acetabular component and illustrating a driver device in broken lines.

FIG. 2 is a side elevational view of FIG. 1 with portions sectioned for illustrative purposes and the driver device accommodated by the instrument.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

As illustrated in the drawings, insertion instrument 10 includes a proximal handle 12 and a distal end 14 interconnected by an arcuate portion 16. Handle end 12 includes a gripping portion 18 which also forms an impaction surface for contact with an impaction instrument. A longitudinal through bore 20 is formed through handle 12. Distal end 14 is generally cylindrical in shape and includes a longitudinal through bore for accommodating a locking bolt 22. Bolt 22 includes a threaded shaft and a head adapted to accommodate a driving instrument such as a screwdriver 24. As illustrated, the longitudinal through bore 20 through handle 12 is aligned with the head of bolt 22 carried by the distal end. Through bore 20 forms a guide means for guiding the shaft of a screwdriver 24 to guide the tip of the screwdriver into the head of bolt 22.

In use, the lock bolt 22 connects the insertion instrument to an acetabular cup 26 for impaction of the cup into the prepared acetabulum of a patient in a known manner. After impaction, the surgeon inserts the shaft of driver 24 through the longitudinal through bore 20 of handle 12 to engage the tip of the driver with the locking bolt.

It should be understood that the invention is not to be limited to the precise details above but may be modified within the teachings of the attached claims.

I claim:

1. An acetabular cup insertion instrument for use in orthopaedic surgery, the instrument comprising, a proximal handle and a distal tip connected by an arcuate intermediate portion in a spaced manner relative to the proximal handle, wherein the proximal handle and distal tip are in longitudinal alignment with one another and the intermediate portion is offset and out of longitudinal alignment with the distal tip and proximal handle, the distal tip including a locking means for connecting the instrument to a prosthetic acetabular implant, the locking means having a head adapted for engagement by a driving member, the proximal handle including a longitudinal through bore extending therethrough, the longitudinal through bore constituting means for accommodating the shaft of a driving member and aligning a tip of the driving member with the head of the locking means.

2. The instrument of claim 1 wherein the longitudinal through bore is aligned with the distal tip of the instrument.

3. An acetabular cup insertion instrument comprising a generally cylindrical proximal handle having a longitudinal through bore therethrough, a distal end spaced from the handle, an arcuate intermediate portion interconnecting the proximal handle and the distal end, the distal end carrying a locking means for engagement with a prosthetic cup, the longitudinal through bore extending through said handle being aligned with the locking means, the through bore constituting guide means for aligning the shaft of a driver device with the locking means to rotate the locking means relative to the distal end, wherein the intermediate portion is laterally spaced from the proximal handle and distal end and out of alignment with the guide means.

4. In combination, an acetabular cup insertion instrument and a driver device, the instrument including a proximal handle having a longitudinal through bore therethrough and a distal end carrying a locking bolt, the distal end and the proximal handle being held in a spaced relationship by an intermediate member wherein a space is defined between the proximal handle and distal end, wherein the proximal handle and distal end are in longitudinal alignment with one another and the intermediate member is offset and out of longitudinal alignment with the distal end and proximal handle, the locking bolt having a head member, the driver device including a shaft terminating in a distal tip configured for mating engagement with the head member of the locking bolt, wherein the shaft of the driver device is accommodated within the through bore of the handle and aligned with the head member of the locking bolt carried by the distal end.

* * * * *